US006849779B1

(12) United States Patent
Messing et al.

(10) Patent No.: US 6,849,779 B1
(45) Date of Patent: Feb. 1, 2005

(54) METHOD FOR PRODUCING HIGH METHIONINE CORN SEEDS

(75) Inventors: Joachim Messing, Somerset, NJ (US); Jinsheng Lai, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/763,329

(22) PCT Filed: Aug. 25, 1999

(86) PCT No.: PCT/US99/20308

§ 371 (c)(1),
(2), (4) Date: Jul. 9, 2001

(87) PCT Pub. No.: WO00/12681

PCT Pub. Date: Mar. 9, 2000

Related U.S. Application Data

(60) Provisional application No. 60/137,836, filed on Jun. 7, 1999, and provisional application No. 60/098,034, filed on Aug. 27, 1998.

(51) Int. Cl.$^7$ .................... C12N 15/82; C12N 15/90; A01H 5/00; A01H 1/00
(52) U.S. Cl. .................... 800/278; 435/468; 800/287
(58) Field of Search ........................ 435/69.1, 320.1, 435/410, 419, 468; 800/278, 287, 295, 298

(56) References Cited

U.S. PATENT DOCUMENTS

| 5,633,436 A | 5/1997 | Wandelt ...................... 800/278 |
| 5,990,384 A | * 11/1999 | Bagga et al. ............... 800/278 |

FOREIGN PATENT DOCUMENTS

| WO | WO 93/08682 | 5/1993 | ............ A01H/1/00 |
| WO | WO 92/14822 | 9/2002 | ........... C12N/15/29 |

OTHER PUBLICATIONS

Hirt et al., Curr. Genet., 1990, vol. 17, pp. 473–479.*
Russel et al., Trans. Res., vol. 6, 1997, pp. 157–168.*
Kirihara et al., Mol. Gen. Genet., vol. 211, 1988, pp. 477–484.*
Sharma, S.B. et al., "Expression of a Sulfur–Rich Maize Seed Storage Protein, δ–Zein, in White Clover (*Trifolium Repens*) to Improve Forage Quality", *Molecular Breeding*, 1998, 4, 435–448, XP–009029886.
Anderson Kirihara, J. et al., "Isolatin and sequence of a gene encoding a methionine–rich 10–kDa protein from maize", *Gene*, 1988, 71, 359–370.
Bagga, S. et al., "Coexpression of the maize zein and β–zein genes results in stable accumulation of –zein in endoplasmic reticulum–derived protein bodies formed by β–zein", *Plant Cell*, 1997, 9, 1683–1696.
Benner, M.S. et al., "Genetic analysis of methionine–rich storage proteins accumulation in maize", *Theoretical & Applied Genetics*, 1989, 78, 761–767.

Ben–Tzvi, T.I. et al., "Lysine and threonine metabolism are subject to complex patterns of regulation in Arabidopsis", *Plant Mol Biol*, 1996, 32, 727–734.
Chaudhuri, S. et al., "Allele–specific imprinting of dzrl, a post–transcriptional regulator of zein accumulation", *Proc. Natl. Acad. Sci. USA*, 1994, 91, 4867–4871.
Chaudhuri, S. et al., "RFLP mapping of the maize dzr1 locus, which regulates methionine–rich 10 kDa zein accumulation", *Mol Gen Genet*, 1995, 246, 707–715.
Christensen, A.H. et al., "Ubiquitin promoter–based vector for high–level expression of selectable and/or screenable marker genes in monocotyledonous plants", *Transgenic Research*, 1996, 5, 213–218.
Chien, C. et al., "A novel RNA–binding motif in influenza A virus non–structural proetin", *Nature Struct. Biol.*, 1997, 4, 891–895.
Chu, C.C. et al., "Establishment of an efficient medium for another culture of rice through comparative experiments on the nitrogen sources", *Sci. Sinica*, 1975, 18,659–668.
Chung, E. et al., "The lysine and sulfur amino acid requirements of two stages of growth in chicks", *J. Nutr.*, 1973, 103, 117–122.
Coleman, C.E. et al., "The maize y–zein sequestors of α–zein and stabilizes its accumulation in protein bodies of tansgenic tobacco endosperm", *Plant Cell*, 1996, 8, 2335–2345.
Cruz–Alvarez, M. et al., "Post–transcriptional regulation of methionine content in maize kernels", *Mol. Gen. Genet.* 1991, 225, 331–339.
Das, O.P. et al., "Molecular methods for genetic analyisis of maize", 1990, *Methods in Molecular and Cellular Biology*, 213–222.
Gordon–Kamm, W.G. et al., "Transformation of maize cells and regeneration of fertile transgenic plants", *The Plant Cell*, 1990, 2, 603–618.
Liu, J. et al., "Crystal structure of the unique multifunctional RNA–binding domain of the influenza virus NS1 protein", *Nature Struct. Bio.*, 1997, 4, 896–899.
Messing, J. et al., "Maternal effect on high methionine levels in hybrid corn", *J. Biotechnol*, 1991, 21, 229–238.

(List continued on next page.)

*Primary Examiner*—Ashwin Mehta
(74) *Attorney, Agent, or Firm*—Woodcock Washburn LLP

(57) ABSTRACT

The present invention provides novel DNA constructs encoding high methionine zein proteins, the expression of which is not negatively regulated by the dzr1 regulatory protein. The constructs of the invention comprise a δ-zein coding region operably linked to a promoter and a 3' UTR which has been modified so as to be devoid of any binding sites for the dzr1 regulatory protein. Preferably, the entire 3' UTR is replaced by a heterologous sequence that does not contain any dzr1 binding sites. Transgenic corn plants comprising the DNA constructs of the invention are also provided. These plants consistently produce high methionine corn seeds.

12 Claims, 8 Drawing Sheets

OTHER PUBLICATIONS

Figure 1:
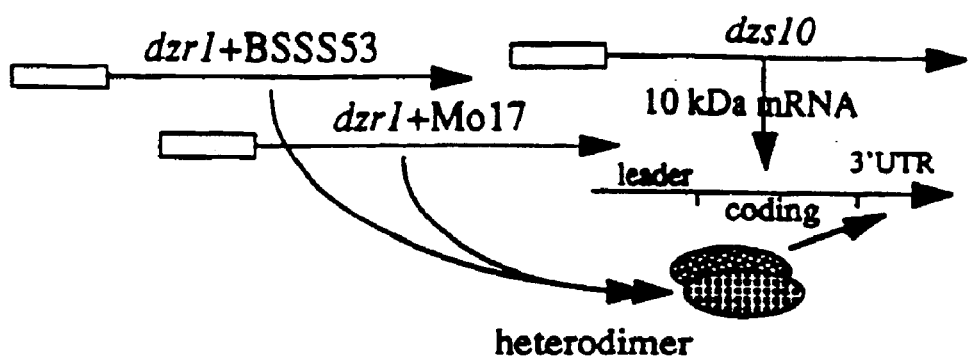

Messing, J. "The manipulation of zein genes to improve the nutritional value of corn", *Trends Biotechnol*, 1983, 1(2), 54–59.

Nawrath, C. et al., Targeting of the polyhydroxybutyrate biosynthetic pathway to the plastids of *Arabidopsis thaliana* results in high levels of polymer accumulation, *Proc. Natl. Acad. Sci. USA*, 1994, 91, 12760–12764.

Pietrzak, et al., Expression in plants of two bacterial antibiotic resistance genes after protoplast transformation with a new plant expression vector, *Nucl. Acids Res*, 1986, 14(14), 5857–5868.

Phillips, R.L. et al., "Elevated protein–bound methionine in seeds of a maize line resistant to lysine plus threonine", *Cereal Chem*, 1985, 62, 213–218.

Rhodes, C.A. et al., Genetically transformed maize plants from protoplasts, *Science*, 1988, 240, 204–207.

Schickler, H. et al., "Repression of the high–methionine zein gene in the maize inbred line Mo17", *The Plant Journal*, 1993, 3, 221–229.

Swarup, S. et al., "Determinants of the high–methionine trait in wld and exotic germplasm may have escaped selection during early cultivation of maize", *Plant J.*, 1995, 8, 359–368.

Ueda, T. et al., "Manipulation of amino acid balance in maize seeds", *Genetic Engineering*, 1993, 15, 109–130.

Ueda, T. et al., "Mutation of the 22– and 27–kd zein promoters affect transactivation by the opaque–2 protein", *The Plant Cell*, 1992, 4, 701–709.

Ueda, T . Et al., "Identification of a transcriptional activator–binding element in the 27–kilodalton zein promoter, the–300 element", Mol Cell. Biol. 1994, 14, 4350–4359.

Wu, L.et al., "3 end processing of the maize 27kDA zein mRNA", *The Plant Journal*, 1993, 4, 535–544.

* cited by examiner

SEQUENCE LISTING

<160> NUMBER OF SEQ ID NOS: 6

<210> SEQ ID NO 1
<211> LENGTH: 972
<212> TYPE: DNA
<213> ORGANISM: Zea mays

<400> SEQUENCE: 1

```
tagaaatatt tgtgttgtat cgaataatga gttgacatgc catcgcgtgt gactcattat      60
taacaataaa acaagtttcc tcttattatc tttttatatc tctccctatc cattttgca     120
aagcccatta tcctttactc cctaagtccc aatatatttt agaccttaaa ttgtatgtct     180
atattcaaaa gaatgacaat aaatctagac atatatataa aacacataca ttaagtattg     240
tatgaatcta ttaaaatgct aaaacgacta atattatggg acggagggag tactttatta     300
gtagattaca ttgttatttt ctctattcca aatataagtc tggttttca atcaatcaat      360
atatattacc atgtccaaac attttgaatt atatatctag gtgcagcatc cgtgcacgat     420
cgtaaaagaa gcagtcacgg tgttggtccc aaaaactaat cgtccgttgt cggtcaccta     480
taaagattca tgaagagaac caaaataagg caatataatt aatgtaatat gactcctcct     540
tttgaattac ttaggaataa cataagcaaa caaaaaagg agaagatcaa ggtaaataaa      600
ggcattttgt gagaaaacat ggaagcataa gaatgcataa gtaatgattt gtgtctcttt     660
atatttttt tattcacgtg aatttacata gataccatcg gatgttcgat ggtaatacaa      720
tgatgcctta gctccgagag cttcgaatga tgagcgattt aaaaatactc ctatcaattg     780
ttcgaaagtt cttttgtctca tgcatgggca atgtacctct atttataggg acggtgcgac    840
gtacaaattt gtataaaatt atattttat tcccaaatcc tatgcatatg tgtcggggac     900
cataattagg ggtaccctca aggctcctaa ttctcagctg gtaaccccat cagcataaag    960
ctgcaaaggc ct                                                         972
```

<210> SEQ ID NO 2
<211> LENGTH: 456
<212> TYPE: DNA
<213> ORGANISM: Zea mays

<400> SEQUENCE: 2

```
ccatggcagc caagatgctt gcattgttcg ctctcctagc tctttgtgca agcgccacta      60
gtgcgaccca tattccaggg cacttgccac cagtcatgcc attgggtacc atgaacccat     120
gcatgcagta ctgcatgatg caacagggc ttgccagctt gatggcgtgt ccgtccctga     180
tgctgcagca actgttggcc ttaccgcttc agacgatgcc agtgatgatg ccacagatga     240
tgacgcctaa catgatgtca ccattgatga tgccgagcat gatgtcacca atggtcttgc     300
cgagcatgat gtcgcaaata atgatgccac aatgtcactg cgacgccgtc tcgcagatta     360
tgctgcaaca gcagttacca ttcatgttca acccaatggc catgacgatt ccacccatgt     420
tcttacagca acccttgttt ggtgctgcat tctaga                                456
```

<210> SEQ ID NO 3
<211> LENGTH: 1102
<212> TYPE: DNA
<213> ORGANISM: Zea mays

<400> SEQUENCE: 3

```
cgtcccgcgt caatattatt aaaaaactcc tacatttctt tataatcaac ccgcactctt      60
```

-continued

```
ataatctctt ctctactact ataataagag agtttatgta caaaataagg tgaaattatg        120
tataagtgtt ctggatattg gttgttggct ccatattcac acaacctaat caatagaaaa        180
catatgtttt attaaaacaa aatttatcat atatcatata tatatatata catatatata        240
tatatatata taaaccgtag caatgcacgg gcatataact agtgcaactt aatacatgtg        300
tgtattaaga tgaataagag ggtatccaaa taaaaaactt gttcgcttac gtctggatcg        360
aaaggggttg gaaacgatta aatctcttcc tagtcaaaat tgaatagaag gagatttaat        420
ctctcccaat ccccttcgat catccaggtg caaccgtata agtcctaaag tggtgaggaa        480
cacgaaacaa ccatgcattg gcatgtaaag ctccaagaat ttgttgtatc cttaacaact        540
cacagaacat caaccaaaat tgcacgtcaa gggtattggg taagaaacaa tcaaacaaat        600
cctctctgtg tgcaaagaaa cacggtgagt catgccgaga tcatactcat ctgatataca        660
tgcttacagc tcacaagaca ttacaaacaa ctcatattgc attacaaaga tcgtttcatg        720
aaaaataaaa taggccggac aggacaaaaa tccttgacgt gtaaagtaaa tttacaacaa        780
aaaaaaagcc atatgtcaag ctaaatctaa ttcgttttac gtagatcaac aacctgtaga        840
aggcaacaaa actgagccac gcagaagtac agaatgattc cagatgaacc atcgacgtgc        900
tacgtaaaga gagtgacgag tcatatacat ttggcaagaa accatgaagc tgcctacagc        960
cgtctcggtg gcataagaac acaagaaatt gtgttaatta atcaaagcta taaataacgc       1020
tcgcatgcct gtgcacttct ccatcaccac cactgggtct tcagaccatt agctttatct       1080
actccagagc gcagaagaac cc                                                1102

<210> SEQ ID NO 4
<211> LENGTH: 1839
<212> TYPE: DNA
<213> ORGANISM: Zea mays

<400> SEQUENCE: 4
aagcttgcat gcctgcaggt ccgtcccgcg tcaatattat taaaaaactc ctacatttct         60
ttataatcaa cccgcactct tataatctct tctctactac tataataaga gagtttatgt        120
acaaaataag gtgaaattat gtataagtgt tctggatatt ggttgttggc tccatattca        180
cacaacctaa tcaatagaaa acatatgttt tattaaaaca aaatttatca tatatcatat        240
atatatatat acatatatat atatatatat ataaaccgta gcaatgcacg ggcatataac        300
tagtgcaact taatacatgt gtgtattaag atgaataaga gggtatccaa ataaaaaact        360
tgttcgctta cgtctggatc gaaaggggtt ggaaacgatt aaatctcttc ctagtcaaaa        420
ttgaatagaa ggagatttaa tctctcccaa tccccttcga tcatccaggt gcaaccgtat        480
aagtcctaaa gtggtgagga cacgaaacaa ccatgcatt ggcatgtaaa gctccaagaa        540
tttgttgtat ccttaacaac tcacagaaca tcaaccaaaa ttgcacgtca agggtattgg        600
gtaagaaaca atcaaacaaa tcctctctgt gtgcaaagaa acacggtgag tcatgccgag        660
atcatactca tctgatatac atgcttacag ctcacaagac attacaaaca actcatattg        720
cattacaaag atcgtttcat gaaaaataaa ataggccgga caggacaaaa atccttgacg        780
tgtaaagtaa atttacaaca aaaaaaaagc catatgtcaa gctaaatcta attcgtttta        840
cgtagatcaa caacctgtag aaggcaacaa aactgagcca cgcagaagta cagaatgatt        900
ccagatgaac catcgacgtg ctacgtaaag agagtgacga gtcatataca tttggcaaga        960
aaccatgaag ctgcctacag ccgtctcggt ggcataagaa cacaagaaat tgtgttaatt       1020
```

```
                                                        -continued aatcaaagct ataaataacg ctcgcatgcc tgtgcacttc tccatcacca ccactgggtc     1080
ttcagaccat tagctttatc tactccagag cgcagaagaa cccggactct agaggatccc     1140
ccatggcagc caagatgctt gcattgttcg ctctcctagc tctttgtgca agcgccacta     1200
gtgcgaccca tattccaggg cacttgccac cagtcatgcc attgggtacc atgaacccat     1260
gcatgcagta ctgcatgatg caacaggggc ttgccagctt gatggcgtgt ccgtccctga     1320
tgctgcagca actgttggcc ttaccgcttc agacgatgcc agtgatgatg ccacagatga     1380
tgacgcctaa catgatgtca ccattgatga tgccgagcat gatgtcacca atggtcttgc     1440
cgagcatgat gtcgcaaata atgatgccac aatgtcactg cgacgccgtc tcgcagatta     1500
tgctgcaaca gcagttacca ttcatgttca acccaatggc catgacgatt ccacccatgt     1560
tcttacagca accctttgtt ggtgctgcat tctagagtcg acctgcaggc atgcaagctc     1620
gagtttctcc ataataatgt gtgagtagtt cccagataag ggaattaggg ttcttatagg     1680
gtttcgctca cgtgttgagc atataagaaa cccttagtat gtatttgtat ttgtaaaata     1740
cttctatcaa taaatttct aattcctaaa accaaaatcc agtactaaaa tccagatcac     1800
ctaaagtccc tatagatccg aattcgcggc cgcaagctt                            1839

<210> SEQ ID NO 5
<211> LENGTH: 133
<212> TYPE: DNA
<213> ORGANISM: Zea mays

<400> SEQUENCE: 5
atattgcatt acaaagatcg tttcatgaaa aataaaatag gccggacagg acaaaaatcc       60
ttgacgtgta aagtaaattt acaacaaaaa aaaagccata tgtcaagcta aatctaattc      120
gttttacgta gat                                                         133

<210> SEQ ID NO 6
<211> LENGTH: 31
<212> TYPE: DNA
<213> ORGANISM: Zea mays

<400> SEQUENCE: 6
tcaagctaaa tctaattcgt tccacgtaga t                                      31
```

METHOD FOR PRODUCING HIGH METHIONINE CORN SEEDS

CROSS REFERENCE TO RELATED APPLICATION

This is the U.S. National Stage filing of PCT/US99/20308, which claims benefit of U.S. provisional application 60/098,034 filed Aug. 27, 1998 and 60/137,836 filed Jun. 7, 1999.

FIELD OF THE INVENTION

This invention relates to agricultural molecular biology to improve the nutritional quality of maize and other cereal crops. In particular, this invention provides a consistently highly expressed zein gene that produces a high methionine seed storage protein.

BACKGROUND OF THE INVENTION

Various scientific and scholarly articles are referred to in parentheses throughout the specification, with full citations appearing at the end of the specification. These articles are incorporated by reference herein to describe the state of the art to which this invention pertains.

The major seed storage proteins of maize are referred to as zeins. In normal maize genotypes, zeins constitute 50–60% of the total endosperm protein at maturity. Zeins are a heterologous group of proteins that can be classified by sequence homology and size (reviewed in Ueda, T. and Messing, J., 1993). The α zeins are the largest subgroup (zein-1), encoded by about 65 genes, and soluble in ethanol under nonreducing conditions. Most of these have a molecular weight of 19 kDa, with one subfamily having a molecular weight of 22 kDa. The other subgroup (zein-2) consists of the β, γ and δ zeins that are soluble in ethanol under reducing conditions. They differ in amino acid composition and sequence homologies.

One δ zein gene encoding a 15 kDa zein has been cloned. This zein was found to encode a protein with a moderate level of methionine (11%). Two cloned γ zeins of 16 and 27 kDa molecular weight were found to be very high in proline. Two δ zeins have been cloned, encoding 10- and 18-kDa proteins rich in methionine (22%, Anderson Kirihara et al., 1988, and 28%, Swarup et al., 1995).

As determined from genetic studies, zeins are regulated at the transcriptional and post-transcriptional level. Differences in regulation occur in a subfamily-specific manner. For instance, opaque-2 (o2) variants prevent the transcriptional activation of 22-kDa α zein genes. Also, as described in more detail below, the dzr1 locus regulates the accumulation of 10-kDa δzein mRNA (Cruz-Alvarez et al., 1991; Schickler et al., 1993).

Like many cereal storage proteins, zeins are deficient in lysine, tryptophan and methionine. For this reason, corn meals used in animal feeds (particularly for monogastric livestock such as poultry) are supplemented with legume (mainly soy) meals to increase the levels of lysine. However, the corn-legume mixture is still deficient in methionine, and processed methionine is often added as a supplement to this mixture. Similarly, it is likely that the methionine level is limited in cereal-legume mixtures, comprising human diets in many third-world communities. Supplementation of cereal-legume mixtures with processed methionine is costly (estimated at about one billion dollars for the U.S. feed business), and in many instances, infeasible. Improving the amino acid composition of maize and other cereals to include more lysine, tryptophan and methionine is therefore an important agronomic objective. Even modest increases in one or more of these amino acids, particularly methionine, in maize and other cereals could lead to a reduced need for processed methionine supplements or added soybean meal.

One approach to producing animal feed with an increased methionine content is to genetically engineer the feed plant (e.g., maize or soybeans) to produce or retain more methionine. Since composition and differential accumulation of various storage proteins, rather than amino acid biosynthesis, is the limiting step, it is the seed proteins themselves that must be engineered, either for altered composition or for enhanced expression.

Using natural variation and crosses of variant inbred lines, Messing and Fisher (1991) produced a maize hybrid, BSSS53xMo17 having a five-fold enrichment of methionine in the prolamin fraction, as compared to the reciprocal hybrid Mo17xBSSS53 with Mo17 as the female parent, sufficient to replace the processed methionine supplement in a soybean-corn diet. When such an enriched diet was tested in a two-week feeding trial of one-day-old chicks, the high methionine maize was demonstrated as a nutritious protein source. The increase in methionine in these hybrid seeds was the result of increased expression of the 10-kDa δ zein gene.

In spite of the successful production of the high methionine BSSS53xMo17 maize hybrid, most hybrids, like the reciprocal cross of Mo17xBSSS53, exhibit an inhibition of the overexpression of the 10-kDa zein gene, by a heretofore unknown mechanism, thereby preventing the use of the high methionine (HM) phenotype for animal feed. Genetic analysis has revealed three single loci related to the HM phenotype (Benner et al, 1989; Swarup et al., 1995): (1) the 10-kDa δ zein locus (dzs 10, delta zein structural gene 10) on the long arm of chromosome 9, the 18-kDa δ zein locus (dzs 18) on the long arm of chromosome 6, and the dzr1 (delta zein regulatory gene 1) formerly called Zpr10/22, on the short arm of chromosome 4. Certain alleles of dzr1 provided the first example in which zein gene expression is controlled by parental imprinting (Chaudhuri and Messing, 1994).

Transcriptional run-on experiments indicate that the lower level of expression of the 10-kDa zein gene in Mo17, as compared to BSSS53, is due to mRNA accumulation rather than transcription (Schickler et al., 1993). This differential expression was found to be due to different alleles of drz1 (Chaudhuri and Messing, 1994). Moreover, heteroallelic combinations of these two alleles result in reduced 10-kDa mRNA levels, indicating that the drz1+Mo17 allele is a negative dominant allele. The result of the presence of this negative dominant allele in Mo17 or any other inbred variety bearing the allele is that hybrids generated therefrom will have reduced expression of the 10-kDa zein gene, even if the other parent overexpresses the gene, either naturally or by genetic engineering.

As an example, U.S. Pat. No. 5,508,468 to Lundquist et al. discloses a fertile hybrid transgenic maize plant regenerated from immature embryos of a cross between A188 and B73, transformed with a chimeric 10-kDa zein gene controlled by the promoter for a 27-kDa zein gene. If such a plant is crossed with Mo17 or any other variety carrying the dominant negative allele of dzr1, any overexpression of the 10-kDa zein transgene (or native gene) that might be seen in the parent will be reduced or lost in the progeny, due to the presence of the dominant negative dzr1 allele.

Clearly, the presence of the negative dominant dzr1 allele is detrimental to the use of a 10-kDa zein gene for increasing methionine content in maize or any other plant. It would be of agronomic and economic significance, then, to identify the mechanism(s) by which the negative allele functions, and to devise methods and biological molecules to circumvent or alleviate such function. On the other hand, circumstances can be envisioned by which the negative function is desirable. Certain gene products that are highly expressed throughout plant development should be specifically reduced during seed maturation and therefore prevented from entering the food chain. Such an example might be the *Bacillus thuringiensis* insecticidal protein, which is needed for insect damage protection but not in the seed flour.

SUMMARY OF THE INVENTION

According to one aspect of the present invention, a DNA construct is provided that encodes a δ-zein which is expressed regardless of the presence of a dominant negative dzr1 allele in the genome. The construct comprises a δ-zein coding sequence operably linked to a promoter and to a sequence encoding a modified 3' untranslated region (UTR), the 3' UTR being modified so as to be devoid of binding sites for a dzr1 negative regulatory protein. In a preferred embodiment, the modified 3' UTR is produced by replacing the sequence encoding the dzr1 binding site-containing 3'UTR with a heterologous sequence encoding a 3' UTR devoid of those binding sites (e.g., the 3' UTR-encoding sequence from a CaMV 35S gene). In another embodiment, the modified 3' UTR is produced by site-directed mutagenesis of sequences encoding the binding sites, so as to destroy the binding sites without affecting the other regulatory functions of the 3' UTR.

In preferred embodiments, the DNA construct contains a coding region encoding a δ-zein selected from the group consisting of a 10 kDa zein and an 18 kDa zein. The promoter preferably is a seed-specific promoter, and may be selected from the group consisting of a 27 kDa zein gene promoter, a 27 kDa (O2) zein gene promoter, a 10 kDa zein gene promoter and an 18 kDa zein gene promoter.

According to another aspect of the invention, a vector for transforming a plant cell is provided, which comprises the DNA construct described above. A plant cell transformed with that vector, and a fertile, transgenic plant regenerated from the transformed cell are also provided.

According to another aspect of the invention, a chimeric gene encoding a 10 kDa zein is provided. The chimeric gene comprises a 10 kDa zein coding region operably linked at its 5' end to a promoter, and to its 3' end to a heterologous 3' UTR. Preferably, the promoter is selected from the group consisting of a 27 kDa zein gene promoter, a 27 kDa (O2) zein gene promoter, a 10 kDa zein gene promoter and an 18 kDa zein gene promoter. Most preferably, the chimeric gene comprises a 10 kDa zein coding region operably linked to a 27 kDa zein gene promoter (or a 27 kDa (O2) promoter) and a CaMV 35S gene 3' UTR. A vector comprising such a chimeric gene is exemplified herein by plasmid pJM2710. A fertile transgenic corn plant which expresses this chimeric gene is also provided.

According to another aspect of the present invention, a method of making high methionine corn seeds is provided. The method comprises the steps of (a) producing a fertile transgenic corn plant expressing the DNA constructs or chimeric genes described above; (b) growing the plant; and (c) harvesting seeds from the plant. Because such plants consistently express the 10 kDa zein, which has a high methionine content, seeds produced therefrom will be consistently enriched in methionine, as compared with equivalent non-transgenic plants, or as compared with transgenic plants expressing a δ-zein that is negatively regulated by the dzr1 regulatory protein. Moreover, the 10 kDa zein produced in such plants appears to be stabilized in protein bodies.

According to another aspect of the invention, an isolated nucleic acid comprising a 3' untranslated region of a 10-kDa zein gene is provided, along with the use of the nucleic acid for dzr1-mediated negative regulation of a coding sequence to which it is operably linked. Preferably, the 3' UTR comprises SEQ ID NO:1. In another preferred embodiment, the coding region codes for a gene product that is undesirable in the seeds (e.g., Bt insecticidal protein).

Other features and advantages of the present invention will be understood from the drawings, detailed description and examples that follow.

BRIEF DESCRIPTION OF THE DRAWINGS

FIG. 1. Schematic diagram showing a proposed mechanism by which dzr1 could function in an allele-specific manner. dzr1+BSSS53 refers to the dzr1 allele carried on the HM phenotype variety BSSS53; dzr1+Mo17 refers to the negative dominant dzr1 allele carried on variety Mo17.

FIG. 2. Construction of plasmids pJM2710 and pJM2710 (O2)). The chimeric gene comprises the 5' regulatory sequences of the 27-kDa zein gene (Z27 promoter or Z27 (O2) promoter), the coding region of the 10-kDa zein gene (Z10 coding) and the 3' untranslated region of the CaMV 35S gene (35S poly A). The chimeric gene is inserted into plasmid pUC119.

FIG. 3. Southern blot analysis of transgenic maize plants. Genomic DNA was isolated from leaf tissue and subjected to Southern blot analysis as described in Example 3. Lanes 1–5 represent samples of Basta-resistant plants; lanes 6 and 7 represent the non-transgenic parents; lane 8 is a size marker with a 1.6 kb band and lane 9 shows the restricted plasmid DNA prior to transformation. All transgenic plants show the diagnostic 1.4 kb fragment derived from the bar gene.

FIG. 4. Northern blot of RNA isolated from immature endosperm of parental and transgenic plant lines. Lane 1, BSSS53 18 days after pollination (DAP); lane 2, Mo17 (18 DAP); lane 3, transgenic line (18 DAP); lane 4, BSSS53 X transgenic line (18 DAP); lane 5, Mo17 X transgenic line (15 DAP); lane 6, Mo17 X transgenic line (18 DAP); lane 7, Mo17 X transgenic line (21 DAP); lane 8, Mo17 X transgenic line (24 DAP); lane 9, Mo17 X BSSS53 (15 DAP); lane 10, Mo17 X BSSS53 (18 DAP); lane 11, Mo17 X BSSS53 (21 DAP); lane 12, Mo17 X BSSS53 (24 DAP) but degraded.

FIG. 5. Western blot showing accumulation of 10-kDa zein in transgenic and parental maize lines. After regeneration of fertile transgenic plants, they were selfed and grown to maturity. Zeins were extracted from seeds following standard protocols, separated by SDS PAGE, blotted to a filter and analyzed with a zein antibody as described previously (Chaudhuri & Messing, 1994). Samples were loaded in the following order: lane 1, transgenic parent; lane 2, Mo17; lane 3, BSSS53; lane 4, Mo17 X BSSS53; lane 5, BSSS53 X Mo17; lane 6, Mo17 X transgenic line; lane 7, transgenic line X Mo17.

FIG. 6. Histogram showing transcription rates of 10-kDa zein gene driven by 27-kDa (Construct #1) or 27-kDa (O2) (Construct #2) promoter. Grey bars selfed transgenic plant using construct #2; black bars Mo17 X transgenic, using Construct #2; white bars=Mo17 X transgenic, using Construct #1. Labeled RNA was hybridized to one of three probes, corresponding to (a) the endogenous 10-kDa zein gene (int 10-kDa), (b) the chimeric 10-kDa zein gene 3'UTR transgene (ext 10-kDa) or (c) as a control, the 15-kDa zein gene (15-kDa).

Figure 7:

FIG. 7. Western blot showing accumulation of 10-kDa zein in parental and transgenic plants. Lane 1, A654 harboring a null mutation of the internal 10-kDa zein gene; lane 2, Mo17; lane 3, BSSS53; lane 4, hybrid parental line used for the transformation; lanes 5 and 6, transgenic plants transformed with a gene controlled by construct #1; lanes 7–9, transgenic plants transformed with a gene controlled by construct #2.

Figure 8:
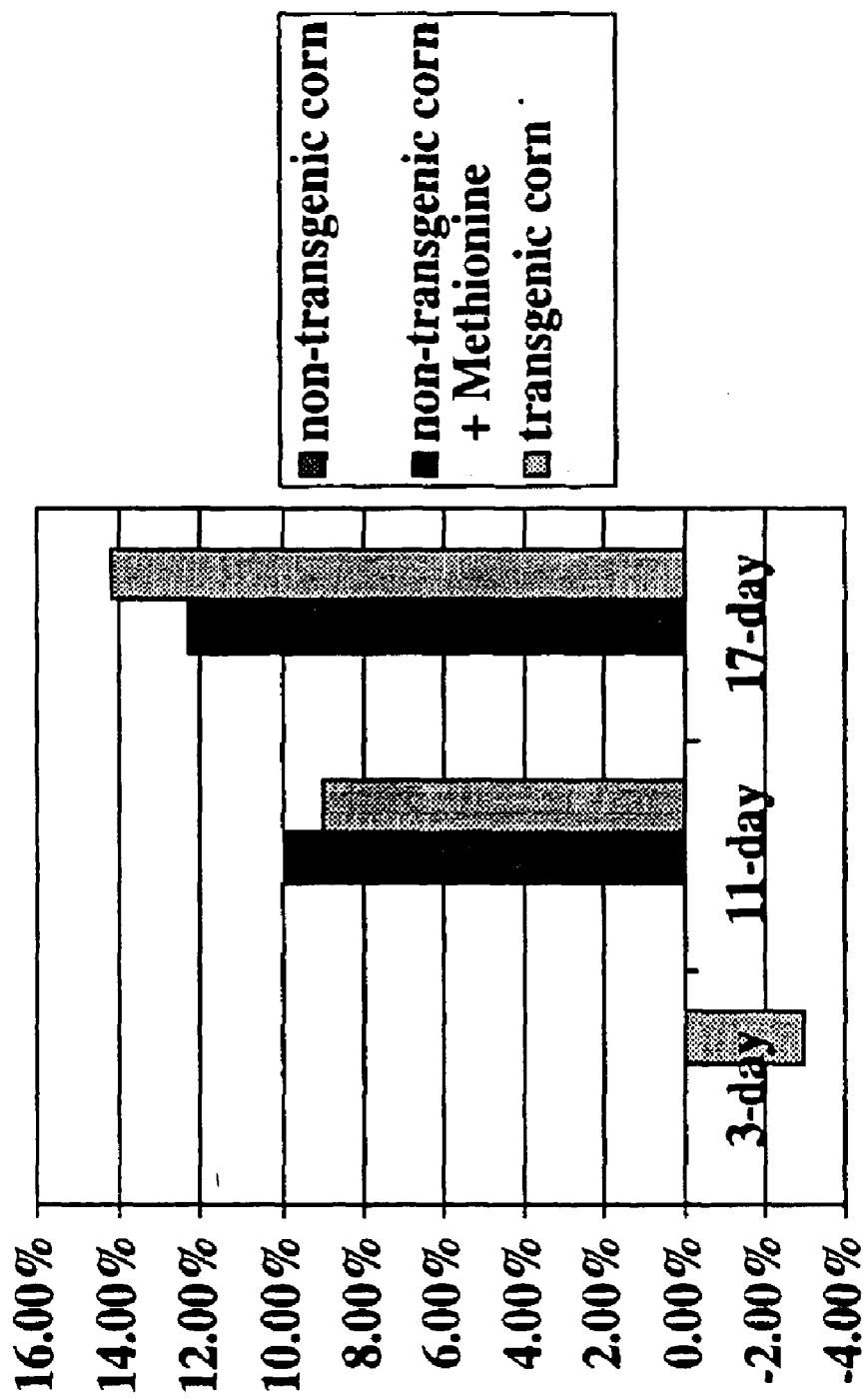

FIG. 8. Histogram showing results of a feeding trial of infant chickens. Groups of chicks were fed (1) inbred corn without methionine supplement (control); or (2) inbred corn with methionine supplement (black bars); or (3) transgenic corn (white bars). Results are expressed as percent weight gain of the test groups (2 and 3) over the control group.

DETAILED DESCRIPTION OF THE INVENTION

II. Definitions

With reference to nucleic acids, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies, the term "immunologically specific" refers to antibodies that bind to one or more epitopes of a protein of interest, but which do not substantially recognize and bind other molecules in a sample containing a mixed population of antigenic molecules.

With respect to oligonucleotides, but not limited thereto, the term "specifically hybridizing" refers to the association between two single-stranded nucleotide molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "promoter region" refers to the 5' regulatory regions of a gene, including promoters, leader sequences and, optionally, enhancers. This term is used interchangeably with the term "5' regulatory region."

The term "3'UTR" or "3' untranslated region" refers to the transcribed portion of a gene following the stop codon. The term "heterologous 3' UTR" refers to a 3' UTR from a source other than the 3' UTR that occurs naturally in a gene. For example, in a preferred embodiment of the present invention, the naturally occurring 3' UTR of the 10 kDa zein gene is replaced with the 3' UTR from the CaMV 35S gene.

The term "reporter gene" refers to genetic sequences which may be operably linked to a promoter region forming a transgene, such that expression of the reporter gene coding region is regulated by the promoter and expression of the transgene is readily assayed.

The term "selectable marker gene" refers to a gene product that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

The term "DNA construct" refers to genetic sequence used to transform plants and generate progeny transgenic plants. These constructs may be administered to plants in a viral or plasmid vector. The biolistic process of transformation is preferred for practice of the present invention. Other methods of delivery such as *Agrobacterium* T-DNA mediated transformation and transformation using electroporation are also contemplated to be within the scope of the present invention. The transforming DNA may be prepared according to standard protocols such as those set forth in "Current Protocols in Molecular Biology", eds. Frederick M. Ausubel et al., John Wiley & Sons, 1995.

The term "genotype" refers to the individual genetic background of each maize variety. The genotype of each variant (e.g. BSSS53) in respect to seed methionine levels can be determined by its "HM or high methionine phenotype." The HM phenotype is recognized by the levels of 10-kDa zein mRNA in immature maize seeds and the 10-kDa zein protein in mature seeds. Once dzr1 has been cloned, DNA finger printing methods can be used to correlate the molecular basis of a genotype with its corresponding phenotype. Two different genotypes that map to the same chromosomal location are referred to as "alleles." To distinguish between different dzr1 alleles, the name of each variant is added (e.g dzr1+BSSS53).

II. Description

In accordance with the present invention, a solution has been found to achieve genotype-independent overexpression of the 10-kDa zein gene. Unlike other methods using different promoters or modifying genes by codon usage, this invention modifies the 3'UTR of a gene, e.g., by replacing it. Therefore, the mRNA can no longer be negatively regulated by trans-acting factors present in many elite lines of corn. As a result of this discovery, novel DNA constructs for transforming plants with a 10-kDa zein gene have been made, which circumvent the function of the dzr1 negative dominant allele. Transgenic plants comprising these novel constructs consistently express the 10-kDa transgene, even in the presence of the negative dominant dzr1 allele.

As mentioned, the lower level of expression of the 10-kDa zein gene in maize variety Mo17, which carries a negative dominant dzr1 allele, is due to mRNA accumulation rather than transcription. It has been discovered in accordance with this invention that, unexpectedly, drz1 influences the accumulation of the 10-kDa mRNA by presumably interacting with the 3'UTR of the mRNA, rather than the 5' regulatory sequences, as is usually the case, since modification of the 3'UTR in fertile transgenic corn plants leads to increased levels of 10-kDa zein protein. Without intending to be limited by any explanation of this phenomenon, it is believed that the allele-specific functionality of drz1 occurs by a mechanism outlined in FIG. 1 and described below, using the HM phenotype of BSSS53 and the negative dominant allele of Mo17 as examples.

Because the transcription rates of 10-kDa zein genes of BSSS53 and Mo17 do not differ, but their steady-state levels of mRNA do, it has been proposed that either a cis- or trans-acting mechanism is responsible for the accumulation of 10-kDa zein mRNA during endosperm development. However, nucleotide sequences of 10-kDa mRNA from either BSSS53 or Mo17 are identical, making a cis-acting mechanism unlikely (Schickler et al., 1993). Genetic mapping experiments have confirmed that the difference between the two mRNA levels is due to a transacting mechanism of a single factor that maps in BSSS53 and Mo17 to the same chromosomal location, but which is different from the location of the 10-kDa zein gene (Chaudhuri and Messing, 1994). Therefore, we surmised that the difference in 10-kDa mRNA accumulation between BSSS53 and Mo17 is due to differences in the trans-acting factor encoded by the same gene. Genes encoding variant products are referred to as alleles. The dzr1+BSSS53 allele produces a factor that gives a HM phenotype, while the dzr1+Mo17 produces one that represses the HM phenotype. More importantly, dzr1+Mo17 is dominant over dzr1+BSSS53.

Although it is not yet fully understood how the dzr1 factor causes the 10-kDa mRNA to accumulate at different levels, one explanation is that dzr1 encodes an RNA-binding protein. If this is the case, then negative dominance by dzr1+Mo17 over dzr1+BSSS53 might imply that such a RNA-binding protein dimerizes prior binding to its target site. In homozygous BSSS53, dzr1 and dzs10 are both transcribed during endosperm development. The gene product of dzr1+BSSS53 would dimerize and bind to the 10-kDa zein mRNA, which would lead to increased accumulation of this mRNA. Increased accumulation of the 10-kDa zein mRNA would lead to more translation of the 10-kDa zein protein. The protein in turn captures more free methionine, resulting in an increased storage of methionine in mature seeds. However, when the dzr1+Mo17 product is made, it heterodimerizes with the dzr1+BSSS51 product. The heterodimer acts like the homodimer of dzr1+Mo17 and causes less 10-kDa zein mRNA to accumulate. As a result, less 10-kDa protein is produced and less methionine captured and stored in mature seed.

Thus, negative dominance indicates that the dzr1 gene product possess at least two domains—one for binding to the 10-kDa mRNA and one for the protein-protein interaction leading to dimerization. Negative dominant allele-encoded homodimers, as well as heterodimers carrying at least one negative-dominant encoded subunit, would act as negative regulators of the 10-kDa zein gene, at the post-transcription level, by virtue of their interaction with the 10-kDa zein mRNA. Since dzr1 has not been cloned yet, it is as yet unknown whether it encodes a RNA-binding protein, and its biochemical properties have not been tested.

Figure 2:
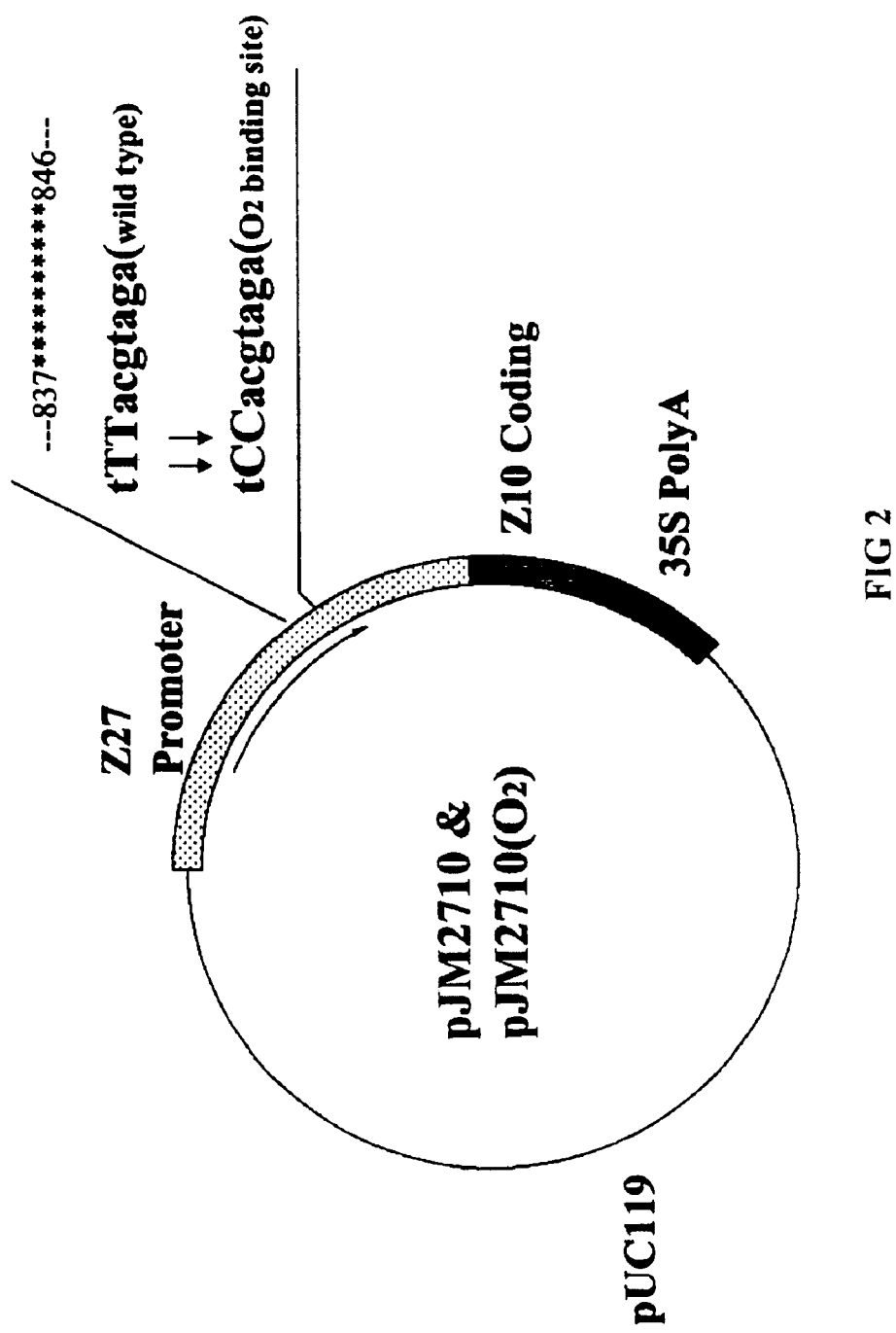

However, cloning of dzr1 is not a prerequisite for manipulating its function. Since we believe that its target is the 10-kDa mRNA, we can modify the primary sequence of the 10-kDa mRNA by modifying the 10-kDa gene. Such a synthetic 10-kDa zein gene is then introduced into the corn genome by DNA transformation methods and tested for its expression in different genotypes including those that carry a negative dominant allele of dzr1. Since the specific site(s) within the 10-kDa mRNA sequence recognized by the dzr1 factor was unknown prior to the present invention, we selected to modify the 3'UTR of the 10-kDa mRNA as our first preference. To include as large a set of possible binding motifs of dzr1 as possible, the 10 kDa zein gene has been completely modified by replacing the 3' UTR (SEQ ID NO:1) with the equivalent region from the CAMV 35S transcript which has been tested in maize protoplasts before (Wu et al., 1994). A preferred construct of this type is shown in FIG. 2 and as SEQ ID NO:4 at the end of the specification. The coding region of the 10-kDa zein gene (SEQ ID NO:2) was operably linked to a 5' regulatory sequence of a 27-kDa zein gene (an exemplary sequence of which is SEQ ID NO:3), and to the 3' UTR of the CaMV 35S transcript. The chimeric gene was inserted into a plasmid that uses the maize ubiquitin promoter and the nos 3' UTR to express the bar gene, the expression of which confers resistance to the herbicide, "Basta" (Fromm et al., 1990; Gordon-Kamm et al., 1990; Christiansen and Quail, 1996).

As described in detail in the examples, a plasmid of this type has been used to transform immature embryos of an A188 X B73 hybrid, using the particle bombardment process. A188 demonstrates low expression of its endogenous 10-kDa zein gene, while B73 exhibits moderately low expression of the gene. Accordingly, a non-transformed A188 (paternal) X B73 (maternal) hybrid should show low accumulation of the endogenous 10-kDa zein. Phosphinotricin-resistant calli have been regenerated into fertile plants, which have either been selfed or backcrossed and grown to maturity. Single seeds have been used to isolate zein proteins for separation by polyacrylamide gel electrophoresis, and zein proteins visualized using specific antibodies. As shown in FIG. 7, in comparison to the parental lines, including the B X A transgenic parent (lane 4), which are low in 10-kDa zein, all of the transgenic seeds exhibit considerable levels of the 10-kDa zein protein. Southern blot analysis of the transgenic plants (FIG. 3) confirms the presence of both the selectable marker gene and the chimeric 10-kDa zein gene, consistent with their herbicide resistance and the accumulation of the 10-kDa zein protein in the mature endosperm. Progeny have been germinated and tested for Basta resistance by a leaf painting assay.

Additional crosses with dominant negative alleles of dzr1 failed to reduce 10-kDa zein levels, indicating an elimination of genetic variability of dzs10 expression (Example 6). Transgenic plants were also used as a replacement for synthetic methionine in an animal feeding trial with excellent results (Example 8).

Transgenic plants differ in their transgenes in three ways. First, independent events place transgenes in different locations of the genome. The so-called position effect has been used to explain variability in tog transgene expression. We have not found any variability of 10-kDa zein protein in a mature seed representing different transformation events, nor observed any gene silencing as described for other cases. Second, independent events differed in the copy number of transgenes. The possibility exists that the higher the copy number the more 10-kDa protein would be made. That is not the case; protein levels are the same regardless of transgene copy number. Third, we have used constructs with two different promoters (Example 7). The 27-kDa zein promoter is known to be a strong seed-specific promoter that is in contrast to the 22-kDa zein promoter not under the control of the b-zip transcription activator Opaque-2 (O2). However, the 27-kDa zein promoter has a sequence motif in the same position as the 22-kDa promoter that resembles the recognition sequence for O2 except for two nucleotides. By using site-directed mutagenesis, we have shown that by repairing these two nucleotides O2 can bind to the 27-kDa promoter, which we call the 27-kDa (O2) promoter (Ueda et al., 1992). Our chimeric gene constructs with the 10-kDa coding region included both 27-kDa promoters. We have tested the two promoters in transgenic corn by transcription run-on assays and found that transcription rates for the 27-kDa (O2) promoter were higher. Therefore, we were able to compare transgenic seeds that differed in the strength of their promoters. Despite different promoter strength, the levels of 10-kDa protein in mature seeds were the same.

All these data indicate that, by removing the negative dominance of dzr1 and by changing promoter strength or gene copy number we find a saturation of protein levels in the seed. The saturation levels of the 10-kDa protein are of important consequence for manipulating corn seed for industrial purposes. The saturation levels are best explained by the compartmentalization of the gene product. Storage proteins are processed and deposited into protein bodies. Any excess of protein that is not deposited is degraded (Coleman et al., 1996; Bagga et al., 1997). Therefore, one can consider the protein body as a detoxification unit of the cell. It is known that overproduction of free amino acids through the manipulation of amino acid biosynthesis causes detrimental symptoms to plant development (Ben-Tzvi et al., 1996). By capturing the free amino acids in proteins that are compartmentalized, these negative effects can be avoided. A similar example exists with other compartments of the cell. Proteins containing a transit peptide are removed from the cytoplasm and transferred into the chloroplast. These proteins can be toxic if they remain in the cytoplasm, but do not cause any problems if they are correctly deposited in the plastids (Nawrath et al., 1994). The efficient compartmentalization may also explain the lack of a position effect and gene silencing, which are frequently associated with variant levels or aberrant gene expression.

Thus, the chimeric 10-kDa zein genes of the present invention enable consistent expression of the 10-kDa zein in any transgenic plant, regardless of its dzr1 allelic composition, by virtue of one critical feature: the native 3' UTR (SEQ ID NO:1) has been modified so that is not the target for dzr1 regulation. This sequence is modified either by replacing it with another 3' UTR or by oligonucleotide site-direct mutagenesis in order to generate chimeric 10-kDa zein genes that are consistently highly expressed in transgenic plants containing them, and progeny thereof. Moreover, transgenic plants expressing these genes produce a predictable and stable amount of 10-kDa zein protein, essentially independent of position effect and transgene copy number.

Furthermore, though at present, dzr1 is known to regulate only dzs10, it may be discovered that the product of this gene also exerts a regulatory effect on other mRNAs, via their 3' UTR target sequences. Accordingly, chimeras of these genes, wherein dzr1 targets are modified to be a non-target, can also be constructed, and are expected to exhibit the same consistent levels of expression. Alternatively, chimeras containing the dzr1 target can be used to down-regulate gene expression. This will be useful in instances where it is desired that a transgene is expressed in other parts of the plant, but not the one entering the food chain. Such an instance may occur if the transgene is a regulatory gene.

Chimeric 10-kDa zein genes of the present invention comprise a 10-kDa coding region, operably linked to native or synthetic 5' regulatory sequences, and modified 3' regulatory region. The coding region may comprise any high-methionine zein encoding sequence. In a preferred embodiment, the coding region of the 10-kDa zein described by Anderson Kirihara et al. (1988) is used. In alternative embodiments, the 18-kDa zein coding region described by Swarup et al. (1995) is used. In other embodiments, coding regions from other genes discovered to be regulated by dzr1 may be used.

Any suitable 5' regulatory region may be used in the chimeric 10-kDa zein gene. For expression of the 10-kDa zein gene, a seed-specific promoter is preferred. In a preferred embodiment, the 27-kDa zein promoter is used. In a particularly preferred embodiment, the 27-kDa(O2)) promoter is used. In another embodiment, the native 10-kDa promoter is used. Other useful promoters include, but are not limited to maize ubiquitin gene promoters, rice actin promoters, maize Adh 1 promoter, rice or maize tubulin (Tub A, B or C) promoters, and alfalfa His 3 promoter. The promoter may be an inducible promoter or one that drives constitutive expression of the gene.

Any suitable, non-native, 3' UTR may be used in the chimeric 10-kDa zein gene. In a preferred embodiment, the 3' UTR from the cauliflower mosaic virus 35S gene is used. In an alternative embodiment, the native 3' UTR may be used, but it must be modified (e.g., by site directed mutagenesis) such that the dzr1 binding sites are removed or replaced, without altering the other regulatory features of the 3' UTR.

Transgenic plants can be generated using standard plant transformation methods known to those skilled in the art. These include, but are not limited to, biolistic DNA delivery (i.e., particle bombardment, *Agrobacterium* vectors, PEG treatment of protoplasts, UV laser microbeam, gemini virus vectors, calcium phosphate treatment of protoplasts, electroporation of isolated protoplasts, agitation of cell suspensions with microbeads coated with the transforming DNA, direct DNA uptake, liposome-mediated DNA uptake, and the like. Such methods have been published in the art. See, e.g., *Methods for Plant Molecular Biology* (Weissbach & Weissbach, eds., 1988); *Methods in Plant Molecular Biology* (Schuler & Zielinski, eds., 1989); *Plant Molecular Biology Manual* (Gelvin, Schilperoort, Verma, eds., 1993); and *Methods in Plant Molecular Biology—A Laboratory Manual* (Maliga, Klessig, Cashmore, Gruissem & Varner, eds., 1994).

The method of transformation depends upon the plant to be transformed. The biolistic DNA delivery method is useful for nuclear transformation of monocotyledenous plants, such as maize, and is preferred for practice of the present invention. Transformation of maize immature embryos using the biolistic method is described in detail in Example 2. In another embodiment of the invention, *Agrobacterium* vectors, particularly superbinary vectors such as described by Ishida et al. (Nature Biotechnology 14:745–750, 1996) are used for transformation of plant nuclei.

Using a biolistic delivery system for transformation, the chimeric gene is linked to a nuclear drug or herbicide resistance marker, such as hygromycin resistance or "Basta" resistance. Biolistic transformation of plant nuclei is accomplished according to the following general procedure:

(1) the gene is inserted into a selected vector;

(2) immature embryos are bombarded with the DNA;

(3) plant tissue is then transferred onto the selective medium to identify transformed tissue; and (4) identified transformants are regenerated to intact fertile plants or are maintained as cultured cells.

Using the chimeric genes and transformation methods described above, transgenic maize plants are produced that express high quantities of the 10-kDa zein seed storage protein. This protein contains a high proportion of methionine codons (23%). Overexpression of this protein in maize seeds increases the capture of free methionine during plant maturation, which otherwise would be lost. Transgenic plants of the present invention are superior to natural high-methionine variants, such as BSSS53 because they consistently express the 10-kDa transgene regardless of the dzr1 allelic composition of the variety. By contrast, combinations of natural HM variants with other germplasms produces a suppression of the high methionine phenotype, rendering the natural variant unreliable for use in commercial corn. Thus, the fertile, chimeric 10-kDa zein transgenic plants of this invention provide a distinct agronomic advantage over HM variants presently available.

As mentioned above, this invention also provides a 31 negative regulatory target of the dzr1 gene product, as exemplified by SEQ ID NO:1. This sequence is expected to be useful for influencing gene expression by negative dominance or once the dzr1 gene is cloned by modified dzr1 factors.

One particularly attractive application for the 3' negative regulatory target of the dzr1 gene product is seed-specific suppression of gene expression, where such suppression would be considered desirable. For instance, insect-resistant transgenic plants are currently being engineered by transforming the plants with the Bt gene, encoding the *Bacillus thuringiensis* insect toxin. For purposes of diffusing or dispelling negative sentiments regarding the safety of such transgenic plants, it may be desirable to reduce expression of the Bt gene in the seeds of the plants. This can be accomplished by operably linking the coding sequence of the gene to the 3' negative regulatory target of the dzr1 gene product. Such a construct would then be subject to dominant negative regulation by dzr1 in seeds of the transgenic plants. The mRNA encoding the Bt protein would be degraded in the endosperm (but not in the other plant parts) and the seeds would remain largely free of Bt toxin.

The following specific examples are provided to illustrate embodiments of the invention. They are not intended to limit the scope of the invention in any way.

EXAMPLE 1

Construction of Plasmid pJM2710

The 27-kDa zein promoter was made by cloning of the 1103 bp PvuI fragment of the 5' flanking sequence of the 27-kDa zein genomic clone, stretching from position −1042 to +61 in respect to the transcriptional start site of the gene as described before (Ueda, T., Messing, J. 1991, Ueda, T. et al, 1994). The 10-kDa zein coding region was made by cutting the 10-kDa genomic clone p10H3 from maize inbred line BSSS53 (Anderson Kirihara, J., Petri, J. and Messing J., 1988) with NcoI and XbaI. This fragment was inserted into the pFF plasmid together with the 203 bp CaMV 35S 3' polyA sequence (Timmermans, M., Maliga P., Vieira J., Messing J., 1990). The resulting plasmid pJM2710 contains three restriction fragments flanked by HindIII sites: the 27-kDa promoter (103 bp), the 10-kDa coding region (465 bp), and the 35S 3'UTR (203 bp). This 1,771 bp HindIII fragment was then inserted into the HindIII site of the transformation vector pUbi-bar by cutting with EcoRI, HindIII and using an adaptor with an EcoRI-NotI-HIndIII site. The final plasmid is as shown in FIG. 2.

EXAMPLE 2

Transformation of Maize with Plasmid pJM2710

Immature embryos with a length of 1.0–2.0 mm were harvested from the maize Hi-II hybrid (parents were obtained from the maize stock center) 14 days after pollination under the sterile condition. Embryos were put on to solidified N6 agar medium supplemented with 1–5 Fg/ml of 2,4-D and then cultured in the dark at 26° C.

Five to seven days after incubation on N6 medium, the embryos were transformed by the particle bombardment method. A Du Pont Biolistic PDS 1000/HE instrument was used for these transformations. The particle samples were coated with 50 Fl of a (50 mg/ml) 1 mm gold particle suspension containing 5–10 Fg purified plasmid DNA and 20 Fl of 0.1 M freshly prepared spermidine and 50 Fl of 2.5 M $CaCl^2$. The DNA-coated particles were precipitated in ethanol, then washed three times and finally resuspended in 30 Fl of anhydrous ethanol. Six Fl of a particle suspension were loaded on a macro carrier. For the bombardment, the membrane rupture pressure was set at 1,300 psi and a 15 mm petri dish with 20 to 30 embryos were put into the chamber 9 cm from the retaining screen and shot twice.

One to two weeks after bombardment, the embryos were transferred to fresh N6 medium with 3 Fg/mL Bialaphos for selection and then kept subcultured every two weeks. After two to three month of selection, resistant calli were grown either for further propagation or regeneration.

Plants were regenerated by placing the resistant calli on regeneration medium (MS or N6, with 2,4-D) under light condition. Multiple plantlets were regenerated from each independent transgenic callus and either selfed, backcrossed to their nontransgenic parents, or outcroseed to another inbred line.

EXAMPLE 3

Southern Blot Analysis of Transgene Integration

Figure 3:
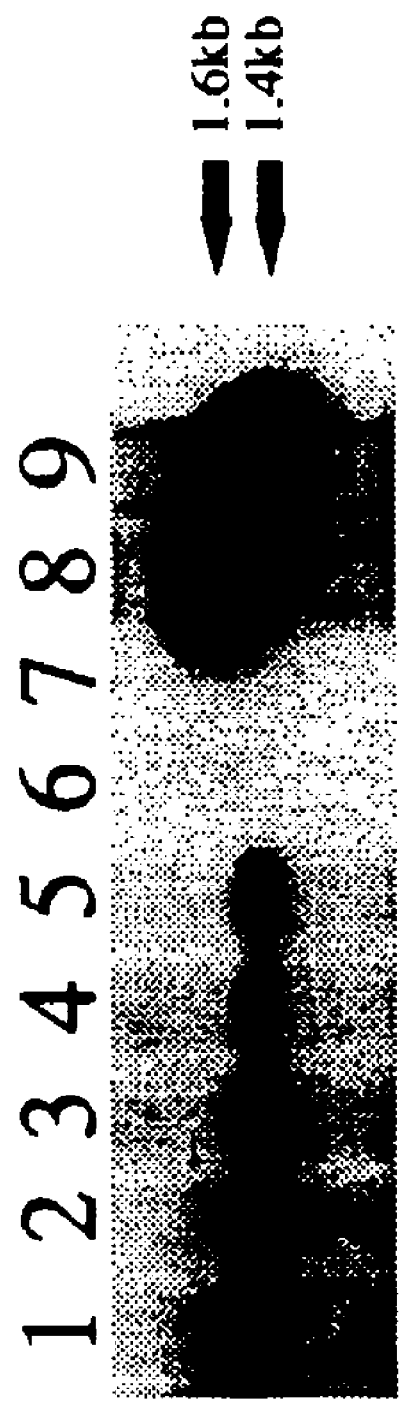

Leaves of primary transformants were collected. Das were extracted in CTAB buffer and digested with EcoRI. The resulting fragments were separated by an 1% agarose gel and transferred to a membrane (Amersham Hybond N). The blot was probed with DNA fragments either representing the 10-kDa rein coding region or the selectable marker gene containing the bar coding region (Pharmacia Labeling Kit). FIG. 3 shows a band of 3.4 kb of the 10-kDa gene and a 1.4 kb fragment of the bar gene in the transgenic plants but not in the nontransgenic control. For the blot probed with the 10-kDa gene, there is a endogenous 10-kDa gene in the

EXAMPLE 4

Testing pJM2710 Transgenic Maize Plants for Expression of the 10-kDa Zein Transgene Mature kernels from sib-crosses and backcrosses to the nontransgenic parents of different transgenic plants were ground to a fine powder and total zeins were extracted in 70% ethanol containing 1% 2-mercapto-enthanol. Based on Peterson's assay for proteins (Peterson, 1977), 2 Fg of total zeins were separated on a 15% SDS polyacrylamide gels and subjected to Western blot analysis according to Chaudhuri and Messing (1994), using 10-kDa antibody. FIG. 7 shows the relative level of 10-kDa expression in transgenic and nontransgenic seeds of inbreds Mo17, A654 and BSSS53.

EXAMPLE 5

Inheritance of Transgene and Segregation Analysis by a Leaf Painting Assay

Mature seeds of sib-crosses and backcrosses from the primary transgenic plants were grown in the field. Second generation analysis of the transgene was performed by following the herbicide tolerance conferred by the selectable marker gene. Expression of this gene was analyzed by applying the herbicide Basta TX (2% v/v, with 0.1% Triton X-100) on small leaf sections. Herbicide resistance was scored six days after application. The resistant plants have leaves as vigorous as untreated plants while the susceptible plants show yellowish and friable leaves. Segregation of transgenic and nontransgenic plants occurs in an outcross with A654 at about 1:1 and in a sib-cross at about 3:1.

EXAMPLE 6

Elimination of Negative Regulation

Figure 4:
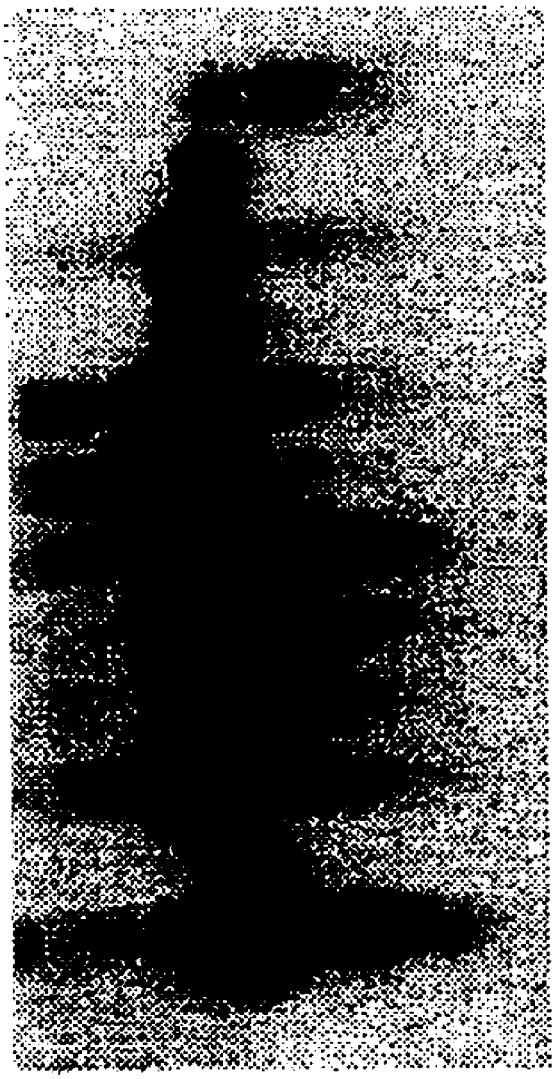

RNA was isolated from immature endosperm of the following plants, then subjected to Northern blot analysis using a 10-kDa zein gene probe: BSSS53, Mo17, a transgenic line, BSSS53 X transgenic line, Mo17 X transgenic line, and Mo17 X BSSS53. Results are shown in FIG. 4. As can be seen, when Mo17 is used as a female with a cross of BSSS53, RNA levels are reduced compared with a cross of Mo17 pollinated with the transgenic line. Crosses with the transgenic line using BSSS53 as the female do not display any difference in 10-kDa mRNA accumulation, as compared to the transgenic line itself.

Storage proteins were isolated from mature seeds and separated by polyacrylamide gel electrophoresis (PAGE). Proteins were blotted and visualized with a 10-kDa zein-specific polyclonal antibody. Cross reaction of the antibody with other zeins served as an internal control.

Figure 5:
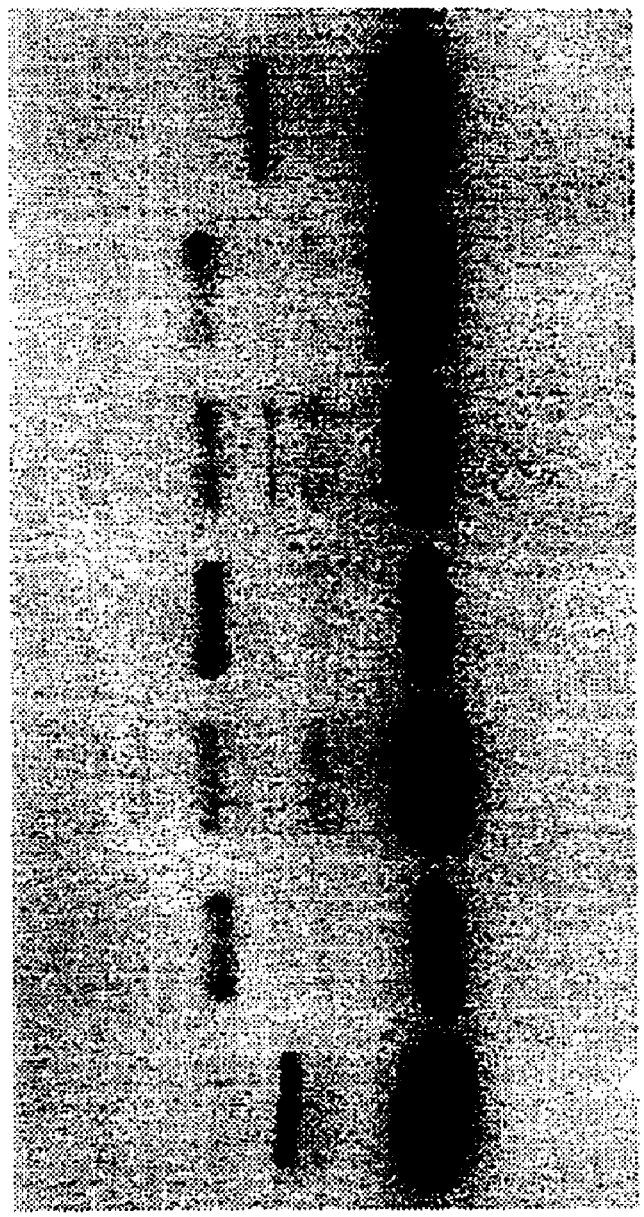

FIG. 5 shows the relative level of 10-kDa protein produced. As can be seen, the transgenic parent exhibited high level expression of the 10-kDa protein, while Mo17, which carries the negative dominant dzr1 allele produced significantly less 10-kDa zein protein. BSSS53, which lacks the negative dominant allele and is a natural overexpresser of the 10-kDa zein gene, exhibited 10-kDa zein protein production similar to the transgenic parent. The hybrid line, when Mo17 was used as a female parent with BSSS53, exhibited a reduction of expression to the level observed for the Mo17 line. In the reciprocal cross when BSSSS53 was used as the female parent, the negative dominant effect was not seen because of genomic imprinting (Chaudhuri and Messing, 1994) and protein levels were comparable to those displayed by the transgenic parent and the BSSS53 line. In the reciprocal crosses of the transgenic line with Mo17, 10-kDa protein expression levels were high regardless of the direction of the cross, as predicted from the Northern blot analysis described above.

EXAMPLE 7

Transcription Rates of 27-kDa and 27-kDa (O2) Promoters in Transgenic Corn

Transcription run-on assays were performed with two constructs that differed by two nucleotides in position -225 and -226, where two T's were replaced by two C's (construct #1 bold and underlined). The sequence TCCA-CAGTAGA (part of construct #2, SEQ ID NO:6) is the canonical binding site for Opaque-2 (O2). We have shown previously by DNA binding assay that O2 binds to the mutated site and that expression of O2 in protoplasts of cultured maize cells leads to a stronger transcription of the 27-kDa (O2) promoter (Ueda et al., 1992). The upstream TGTAAG motif (also bolded and underlined) is the so called prolamin box (PB) which is present in all zein promoters and believed to be a cis-acting site for a general transcription factor (Ueda et al., 1994).

Construct #1 (SEQ ID NO:5) (27-kDa zein promoter region, -349 to -217):

5-ATATTGCATTACAAAGATCGTTTCATGAAAAAT AAAATAGGCCGGACAGGACAAAAATCCTTGA CGTGTAAAGTAAATTTACAACAAAAAAAAGC CATATGTCAAGCTA AATCTAATTCGTTTTAC GTAGAT-3'

Construct #2 (SEQ ID NO:6) (27-kDa (O2) zein promoter region, -248 to -217):

5'-TCAAGCTAAATCTAATTCGTTCCACGTAGAT-3'

Transcription rates of transgenic plants that were either selfed or crossed with Mo17 as the female were, measured at 18 days after pollination when zein gene expression is very high. Nuclei were isolated and labeled as described previously (Cruz-Alvarez et al., 1991; Schickler et al., 1993). Labeled RNA was hybridized to a probe (a) of the endogenous 10-kDa zein gene 3'UTR, (b) the chimeric 10-kDa zein gene 3'UTR (transgene), and (c) the 15-kDa zein.

Figure 6:
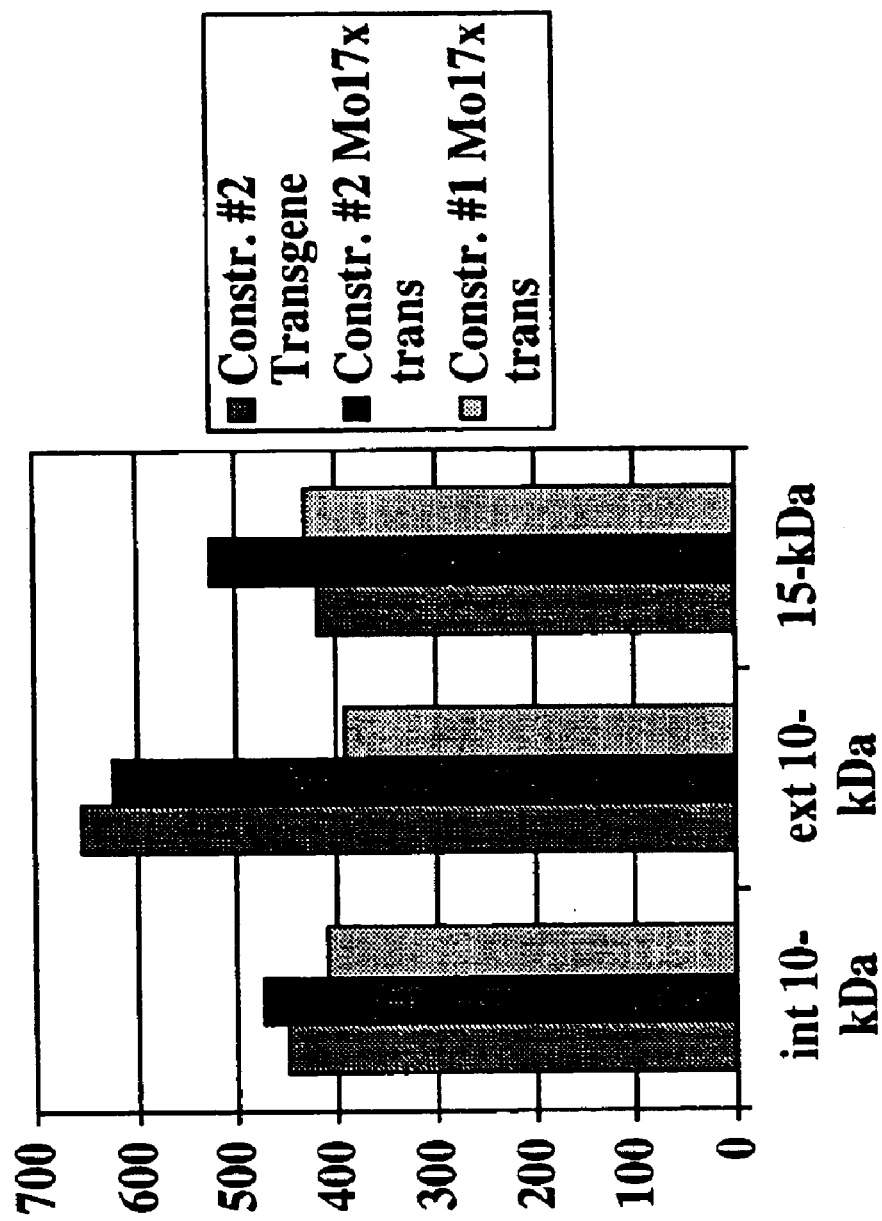

Results are shown in FIG. 6. In all three plants the internal promoters of the 10-kDa and the 15-kDa zein (control) gene showed similar transcription L1 levels. However, transcription levels of construct #2 were higher than construct #1, consistent with the fact that O2 gives rise to transcriptional activation.

Storage proteins were isolated from mature seeds and separated by polyacrylamide gel electrophoresis (PAGE). Proteins were blotted and visualized with a 10-kDa zein-specific polyclonal antibody. Cross reaction of the antibody with other zeins served as an internal control.

Results are shown in FIG. 7. A654, a line carrying a null mutation of the internal 10-kDa zein gene, showed no 10-kDa zein production. Both Mo17, which carries the negative dominant dzr1 allele, and the hybrid parental line that was used for the transformation displayed minimal 10-kDa zein production. In contrast, the BSSS53 that lacks the negative dominant allele and is a natural overexpresser of the 10-kDa zein gene produced a significant amount of the protein, as did transgenic plants transformed with genes controlled by either construct #1 or construct #2.

EXAMPLE 8

Feeding Trial

A feeding trial was conducted with 2-day-old chickens as described previously (Messing and Fisher, 1991). Three groups were fed three types of corn-based diets. In one case, the inbred that serves as a host for transformation experiments was used without methionine supplements (control group) and in the other with methionine supplements (normal group). The third group of animals also did not receive any methionine supplements but the meal from transformed corn containing the transgene of construct#1 (transgenic group). Weight gained during the feeding trial was expressed as percentage of additional weight over the control group.

Results are shown in FIG. 8. The percentage of weight gain in the normal and the transgenic group over the control group was comparable, possibly with a faster gain in the transgenic group. This clearly indicates that the transgenic corn completely replaces the supplemented methionine.

REFERENCES

Anderson Kirihara, J., Petri, J. B., and Messing J. (1988). Isolation and sequence of a gene encoding a methionine-rich 10-kDa protein from maize. Gene 71: 359–370.

Bagga, S., Adams, H. P., Rodriguez, F. D., Kemp, J. D., and Sengupta-Gopalan, C. (1997). Coexpression of the maize δ-zein and β-zein genes results in stable accumulation of δ-zein in endoplasmic reticulum-derived protein bodies formed by β-zein. Plant Cell 9: 1683–1696.

Benner, M. S., Phillips, R. L., Kirihara J. A. and Messing J. W. (1989). Genetic analysis of methionine-rich storage proteins accumulation in maize. Theoretical and Applied Genetics 78: 761–767.

Ben-Tzvi, T. I., Perl, A., and Galili, G. (1996). Lysine and threonine metabolism are subject to complex patterns of regulation in *Arabidopsis*. Plant Mol. Biol. 32: 727–734.

Chaudhuri, S. and Messing, J. (1994). Allele-specific imprinting of dzr1, a post-transcriptional regulator of zein accumulation. Proc. Natl. Acad. Sci. USA 91: 4867–4871.

Chaudhuri, S. and Messing, J. (1995). RFLP mapping of the maize dzr1 locus that regulates methionine-rich 10-kDa zein regulation. Mol. Gen. Genet. 246: 707–715.

Christensen, A. H. and Quail, P. H. (1996). Ubiquitin promoter-based vector for high-level expression of selectable and/or screenable marker genes in monocotyledonous plants. Transgenic Research 5: 213–218.

Chien, C., Tejero, R., Huang, Y, Zimmerman, Krug, R. M. and Montelione, G. T. (1997). A novel RNA-binding motif in influenza A virus non-structural protein, Nature Struct. Biol. 4: 891–895.

Chu, C. C., Wang, C. C., Sun, C. S., C. Hus, C., Yin, K. C. and Chu, C. Y. (1975). Establishment of an efficient medium for anther culture of rice through comparative experiments on the nitrogen sources. Sci. Sinica. 18:659–668.

Chung, E., Griminger, P. and Fisher, H. (1973). The lysine and sulfur amino acid requirements of two stages of growth in chicks. J. Nutr. 103: 117–122.

Coleman, C. E., Herman, E. M., Takasaki, K., and Larkins, B. A. (1996). The maize γ-zein sequesters α-zein and stabilizes its accumulation in protein bodies of transgenic tobacco endosperm. Plant Cell 8: 2335–2345.

Cruz-Alvarez, M., Kirihara J. A. and Messing, J. (1991). Post-transcriptional regulation of methionine content in maize kernels. Mol. Gen. Genet. 225: 331–339.

Das, O. P., Cruz-Alvarez M., Chaudhuri S. and Messing J. (1990). Molecular methods for genetic analysis of maize. Methods in Molecular and Cellular Biology. 213–222.

Gordon-Kamm, W. G., et al, (1990). Transformation of maize cells and regeneration of fertile transgenic plants. The Plant Cell 2: 603–618.

Liu, J., Lynch, P. A., Chien, C., Montelione, G. T., Krug, R. M. and Berman, H. M. (1997). Crystal structure of the unique multifunctional RNA-binding domain of the influenza virus NS1 protein. Nature Struct. Bio. 4: 896–899.

Messing, J. and Fisher, H. (1991). Maternal effect on high methionine levels in hybrid corn. J. Biotechnol. 21: 229–238.

Messing, J. (1983). The manipulation of zein genes to improve the nutritional value of corn. Trends Biotechnol. 1: 1–6.

Nawrath, C., Poirier, Y., and Somerville, C. (1994). Targeting of the polyhydroxybutyrate biosynthetic pathway to the plastids of *Arabidopsis thaliana* results in high levels of polymer accumulation. Proc. Natl. Acad. Sci. USA 91: 12760–12764.

Phillips, R. L. and McClure, B. A. (1985). Elevated protein-bound methionine in seeds of a maize line resistant to lysine plus threonine. Cereal Chem. 62: 213–218.

Rhodes, C. A., Pierce, D. A., Mettler, I. J., Mascarenhas, D., and Detmer, J. J. (1988). Genetically transformed maize plants from protoplasts. Science 240: 204–207.

Schickler, H., Benner M. S., and Messing, J. (1993). Repression of the high-methionine zein gene in the maize inbred line Mo17. The Plant Journal 3: 221–229.

Swarup, S., Timmermans, M. C. P., Chaudhuri, S. and Messing, J. (1995). Determinants of the high-methionine trait in wild and exotic germplasm may have escaped selection during early cultivation of maize. Plant J. 8: 359–368.

Timmermans M, Maliga P. Vieira J, Messing J. (1990). The pFF plasmids: cassettes utilising CaMV sequences for expression of foreign genes in plants. J. Biotechnol. 14: 333–344.

Ueda, T. and Messing, J. (1993). Manipulation of amino acid balance in maize seeds. In: Genetic Engineering, Vol. 15, J. K. Setlow (ed), Plenum Press, New York, 109–130.

Ueda, T., Waverczak, W., Ward, K., Sher, N., Ketudat, M., Schmidt, R., and Messing, J. (1992). Mutations of the 22- and 27-kD zein promoters affect transactivation by the opaque-2 protein. The Plant Cell 4: 701–709.

Ueda, T., Wang, Z., Pham, N. and Messing, J. (1994). Identification of a transcriptional activator-binding element in the 27-kilodalton zein promoter, the −300 element. Mol. Cell. Biol. 14: 4350–4359.

Wu, L., Ueda, T. and Messing, J. (1993). 3=-end processing of the maize 27 kDA zein mRNA. The Plant Journal 4: 535–544.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

We claim:

1. A method of making corn seeds that produce increased amounts of 10 kDa zein and increased methionine content, comprising the steps of:
  a) transforming cells of a dzr1 negative dominant allelic corn plant with a vector comprising a chimeric gene encoding a maize 10 kDa zein, wherein the chimeric gene comprises a maize 10 kDa zein coding region operably linked at its 5' end to a promoter, and at its 3' end to a heterologous 3' UTR, wherein the product of the dzr1 negative dominant allele negatively regulates expression of an endogenous maize 10 kDa zein gene, comprising its native 3' UTR, in said corn plant;
  b) regenerating from the transformed cells a fertile transgenic corn plant expressing the chimeric gene; and
  c) producing seeds comprising the dzr1 negative dominant allele from the plant, wherein the seeds express the chimeric gene and produce increased amounts of the 10 kDa zein, thereby increasing methionine content of said seed.

2. The method of claim 1, wherein the chimeric gene comprises a promoter selected from the group consisting of a 27 kDa zein gene promoter, a 27 kDa (O2) zein gene promoter, a 10 kDa zein gene promoter and an 18 kDa zein gene promoter.

3. The method of claim 2, wherein the chimeric gene comprises a 10 kDa zein coding region operably linked to a 27 kDa zein gene promoter and a CaMV 35S gene 3' UTR.

4. The method of claim 3, wherein the chimeric gene is contained in vector pJM2710.

5. A fertile transgenic corn plant produced by the method of claim 1.

6. The method of claim 1, further comprising the step of breeding the fertile transgenic corn plant with another corn plant to produce progeny corn plants that produce seeds with increased methionine content and comprising said dzr1 negative dominant allele and said chimeric gene.

7. A progeny corn plant that produces seed with increased methionine content, said progeny corn plant produced by the method of claim 6.

8. A fertile, transgenic corn plant that produces corn seeds with increased methionine content, wherein said plant contains a dzr1 negative dominant allele in its genome, and a chimeric gene encoding a maize 10 kDa zein, wherein the chimeric gene comprises a maize 10 kDa zein coding region operably linked at its 5' end to a promoter, and at its 3' end to a heterologous 3' UTR, wherein said seeds comprise the dzr1 negative dominant allele and the chimeric gene.

9. The transgenic corn plant of claim 8, wherein the chimeric gene comprises a promoter selected from the group consisting of a 27 kDa zein gene promoter, a 27 kDa (O2) zein gene promoter, a 10 kDa zein gene promoter and an 18 kDa zein gene promoter.

10. The transgenic corn plant of claim 9, wherein the chimeric gene comprises a maize 10 kDa zein coding region operably linked to a 27 kDa zein gene promoter and a CaMV 35S gene 3' UTR.

11. The transgenic corn plant of claim 10, wherein the chimeric gene is contained in vector pJM2710.

12. A progeny corn plant that produces seed with increased methionine content, said plant produced by breeding the fertile transgenic corn plant of claim 8 with another corn plant, wherein said progeny corn plant comprises said dzr1 negative dominant allele and said chimeric gene.

* * * * *